United States Patent
Pastorello et al.

(10) Patent No.: US 7,709,018 B2
(45) Date of Patent: May 4, 2010

(54) COMPOSITE STRUCTURES CONTAINING HYALURONIC ACID THE DERIVATIVES THEREOF AS NEW BONE SUBSTITUTES AND GRAFTS

(75) Inventors: Andrea Pastorello, Abano Terme (IT); Daniele Pressato, Montegrotto Terme (IT)

(73) Assignee: Fidia Advanced Biopolymers S.R.L., Abano Terme (IT)

( * ) Notice: Subject to any disclaimer, the term of this patent is extended or adjusted under 35 U.S.C. 154(b) by 71 days.

(21) Appl. No.: 10/580,659

(22) PCT Filed: Nov. 26, 2004

(86) PCT No.: PCT/EP2004/053129

§ 371 (c)(1), (2), (4) Date: May 26, 2006

(87) PCT Pub. No.: WO2005/051446

PCT Pub. Date: Jun. 9, 2005

(65) Prior Publication Data

US 2007/0110819 A1 May 17, 2007

(30) Foreign Application Priority Data

Nov. 27, 2003 (IT) .......................... PD2003A0286

(51) Int. Cl.
*A61F 2/00* (2006.01)
*A61K 9/00* (2006.01)
*A61F 13/00* (2006.01)
*A61K 35/32* (2006.01)

(52) U.S. Cl. ...................... 424/423; 424/400; 424/422; 424/549

(58) Field of Classification Search ...................... None
See application file for complete search history.

(56) References Cited

U.S. PATENT DOCUMENTS

| 5,939,323 A * | 8/1999 | Valentini et al. ............ 435/395 |
| 2001/0053938 A1 | 12/2001 | Dorigatti |
| 2004/0076656 A1 | 4/2004 | Pavesio |

FOREIGN PATENT DOCUMENTS

| WO | WO 93/20858 | 10/1993 |
| WO | WO 95/01181 | 1/1995 |
| WO | WO 02/70030 | 9/2002 |

OTHER PUBLICATIONS

Sigma-Aldrich "Hydroxyapatite" Sigma-Aldrich Catalog <http://www.sigmaaldrich.com/catalog/search/ProductDetail/SIAL/289396> accessed online Mar. 17, 2008, 2 pages.*
Bakos et al., "Hydroxyapatite-Collagen-Hyaluronic Acid Composite," Biomaterials 20:191-195, 1999.

* cited by examiner

*Primary Examiner*—Christopher R Tate
*Assistant Examiner*—Aaron J Kosar
(74) *Attorney, Agent, or Firm*—Clark & Elbing LLP

(57) ABSTRACT

A composite material comprising: (i) hyaluronic acid and/or hyaluronic acid derivatives, (ii) demineralised bone and/or biocompatible partially or totally demineralised bone tissue matrix and/or biocompatible and bioresorbable ceramic materials. This material preferably associated with at least one layer comprising a hyaluronic acid derivative may be used in the preparation of bone substitutes or grafts for the regeneration or formation of bone tissue in surgery.

47 Claims, No Drawings

COMPOSITE STRUCTURES CONTAINING HYALURONIC ACID THE DERIVATIVES THEREOF AS NEW BONE SUBSTITUTES AND GRAFTS

CROSS-REFERENCE TO RELATED APPLICATIONS

This application claims priority under 35 U.S.C. §371 from international application PCT/EP2004/053129, filed Nov. 26, 2004, which claims priority from Italian Patent Application PD2003A000286, filed Nov. 27, 2003.

FIELD OF THE INVENTION

The present invention relates to a composite material for use in the preparation in of bone substitutes or grafts for the regeneration or formation of bone tissue in oncological, orthopaedic and spinal surgery.

BACKGROUND OF THE INVENTION

"Backache" affects about 60% of the population aged over 65/70 years, and approximately one third of sufferers have to undergo spinal surgery.

Although the etiology of backache remains partially unexplained, reliable clinical data trace the cause to a slow degenerative process in the intervertebral disk. Such a process may be due to various causes:
altered metabolic activity;
reduced supply of nutrients;
decreased cell viability;
mainly age-related cell senescence.

For the surgical treatment of said pathology, two procedures are currently in use: removal of the disk (diskectomy) and the fusion of the two adjacent vertebrae (spinal fusion).

Vertebrae can be fused together by a special surgical technique that prevents any movement between them.

This type of intervertebral fusion is also performed in other pathologies, namely:
breakage of one or more vertebrae;
to correct spinal deformities such as scoliosis;
Following removal of an intervertebral disk;
Infections and/or tumours that may cause degradation of the vertebral body;
To treat vertebral instability where the vertebrae are prone to slide on one another. This condition is called spondylolisthesis and may cause compression of the nerve roots, so that, besides pain, there may be impaired movement of the upper and lower limbs.

There are various surgical techniques and methods of fusing two adjacent vertebrae but they all involve the introduction/application of a bone graft, generally between two vertebrae, or bone substitutes of various kinds of different shapes and sizes, such as pins, plugs or small plates fitted in the intervertebral spaces to prevent collapse and assist fusion.

Said measures are aimed to:
maintain correct alignment between the two vertebrae;
maintain and reconstruct the intervertebral space;
consolidate fusion;
eliminate pain caused by compression of the nerve root due to slipping or herniation of the disk.

It is known that spinal fusion may also require additional fixing at the back of the two vertebrae, using rigid metal instruments of various kinds and sizes, such as screws, plugs, pins, plates, intervertebral connectors in various materials, with or without a screwable thread (for example, titanium), to prevent the vertebrae from slipping on one another with consequent compression and loss of alignment, while fusion is established.

These devices do not undergo resorption so they generally remain at the site of implantation until they are surgically removed once fusion is complete.

For many years, the material used for bone grafts was of bovine origin, or it was constituted by fragments from the tibia, fibula, femur or iliac crest of autologous or heterologous origin, with a fusion success rate ranging between 63 and 95%.

The fusion process is similar to that which occurs following bone fracture and is not visible on X-ray till six weeks after surgery.

The vertebrae can be fused in the intervertebral space and/or to the front between the two adjacent vertebral bodies and/or to the back between adjacent transverse processes, laminae, or between other posterior elements of the vertebrae, according to the pathology that the surgery in question is intended to treat.

As we have already said, solid fusion is generally achieved by grafting autologous or allogenic bone, both having specific advantages and disadvantages.

Indeed, in the case of autogenous bone, it may prove difficult to find a quantity that is sufficient for the purpose of the graft. Allogenic bone, on the other hand, is sure to have less osteoinductive activities.

These difficulties have led to the study and development of bone substitutes of synthetic, semi-synthetic and bioengineering origin, that is, to the construction of two- and three-dimensional osteoconductive matrices able to induce the migration of cells within their structure for the subsequent formation of bone.

Research was then focused on the study of the physiological mechanisms involved in bone repair and regeneration.

Bone is constituted by cells immersed in an extracellular matrix, 30-35% of the dry weight of which is represented by organic matrix (formed by fibres of collagen and glycosaminoglycans including hyaluronic acid), and inorganic substances (including calcium phosphate, calcium and magnesium fluoride) deposited among the collagen fibrils during the mineralisation phase.

Bone metabolism is regulated by hormones and growth factors mainly released by platelets, macrophages, fibroblasts or other types of cell, and chiefly includes, for example, proteins such as BMP, TGF, PDGF, FGF, EGF, IGF and VEGF that can have both a osteoinductive and angiogenic effect on the mesenchymal cells of bone marrow.

Special three-dimensional matrices have been designed and developed in various forms with different types of polymer, such as poly-L-lactic acid, poly-glycolic acid and poly-lactic-co-glycolic acid, for the formation of scaffolds (possibly containing also trophic and/or osteoinductive factors) that can favour the migration of bone progenitor cells within their structure for the regeneration/formation of new bone tissue (Boyan B D et al., Clin Plast Surg. 1999, 26(4):629-645; Ishaug S L et al., J Biomed Mater Res, 1997, 36(1):17-28).

However, it is known that these polymers can actually be toxic, because they release lactic acid as they degrade, and moreover they may induce an inflammatory response thus inhibiting the bone regeneration process.

Ceramics too, like hydroxyapatite, tribasic calcium phosphate, and calcium sulphate, have been widely used in bone regeneration because they are biocompatible and have osteoinductive potential.

Also known is the use of proteins (and other molecules) of the extracellular matrix for the formation of porous and/or fibrous structures (such as collagen, laminin, fibronectin, and hyaluronic acid) that enhance osteoblast migration and differentiation because they can be loaded with osteoinductive trophic factors.

As we have already said, the main trophic, osteoinductive factors are BMP and TGF, and they are able to direct stem cells to differentiate into osteoblasts and subsequently osteocytes.

BMP was first isolated from demineralised bone specimens. Indeed, as early as 1965, it was demonstrated that such demineralised matrices (DM) induced the formation of new bone structures (Urist M R, Science 150: 893, 1965).

Further studies subsequently clarified the role of BMP in the repair/formation of bone tissue.

In 1990, clinical trials on the fusion of vertebrae using various types of carrier containing BMP, in comparison with autologous bone grafts (Boden S D et al., Spine, 2000, 25(3): 376-381), showed that the protein determined a high fusion rate with consequent increase in the mechanical stability of the fused vertebrae. The process of producing DM consists in pulverising bone samples into particles with a diameter of 70-450 µm prior to partially or totally demineralising them with 0.5 N of HCL.

This process enables the total or partial maintenance of the organic component of the bone tissue, ensuring also the integrity of the proteins (and therefore of the gowth factors) contained therein.

The ability of bone to regenerate when damaged is due to certain peculiar features:
  osteogenic capacity;
  osteoinductive capacity;
  osteoconductive capacity.

In spinal surgery, this last property is linked with the presence of a scaffold fixed to the structures to be fused, allowing the migration and distribution of both bone progenitor and vascular cells within its structure.

It is known that the best examples of scaffolds are autologous and/or allogenic bone grafts, demineralised bone matrices, ceramics, bone substitutes constituted by molecules of extracellular matrix (such as collagen and glycosaminoglycans), even though it is obvious that only bone grafts and DM can be defined as osteoinductive, because of the intrinsic presence of differentiating factors. The osteogenic and osteoconductive potential of the scaffolds listed above can be considerably increased by introducing bone-progenitor cells, possibly derived from:
  whole bone marrow;
  bone marrow treated for the preparation of purified mesenchymal cells (possibly also expanded in vitro);
  bone marrow treated for the preparation of mesenchymal cells expanded in vitro and also partially differentiated towards the induction of osteoblasts using osteoinductive factors such as TGF β1 and BMP.

Various scientific experiments have already demonstrated the validity of the use of autologous and/or allogenic mesenchymal cells loaded into different carriers/scaffolds or into matrices constituted by molecules of the extracellular matrix, or by synthetic and/or semisynthetic polymers, or into ceramics, possibly associated with differentiating factors in the regeneration/formation of new bone tissue (Horwitz E M et al., Nat Med, 1999, 5(3):309-313; Gregory A H et al., Neurosurg Focus, 2001, 10(4):1-5; Pilitsis J G et al., Neurosurg Focus, 2002, 13(6):1-6).

For the above reasons, there are many known types of bone graft for use in spinal orthopaedic, neuro-maxillofacial and dental surgery, in orthopaedic surgery to the shoulder, hand and foot, in oncological surgery and in all those pathologies requiring the regeneration/formation of new bone tissue (hence also in pathologies where the fusion of two adjacent bones is indispensable), such as in the following examples:
  demineralised and freeze-dried bone powder in a simple mixture with glycerol; (U.S. Pat. No. 5,073,373);
  hydrogels constituted by hyaluronic acid or chitosan, cross-linked and with a high molecular weight, containing particles of demineralised bone and possibly also BMP (U.S. Pat. No. 6,326,018);
  porous, biodegradable, three-dimensional matrices, containing a mesh of fibres constituted by mineralised polymers such as collagen immersed in other polymers (such as cellulose, hyaluronic acid, chitosan and others of synthetic origin), and possibly also containing bone marrow cells (U.S. Pat. No. 5,776,193);
  grafts constituted by porous, composite scaffolds, containing hydrophilic materials such as collagen, glycosaminoglycans and other synthetic and/or semisynthetic polymers, as vehicles for proteins such as BMP (EP 0784985);
  bone substitutes constituted by an organic matrix of demineralised bone, subsequently treated with glycosaminoglycans, containing bone-inductive factors for bone regeneration (U.S. Pat. No. 6,165,487);
  artificial bone substitutes mainly formed by collagen in matrices of calcium sulphate (U.S. Pat. No. 5,425,769);
  bone substitutes composed of demineralised bone matrices and poloxamer as carrier;
  porous synthetic matrices containing polymers such as collagen and glycosaminoglycans cross-linked ex vivo, also containing osteogenic proteins and setting agents such as methylcellulose (U.S. Pat. No. 6,468,308);
  bone grafts constituted by particles of demineralised bone, in a carrier containing hyaluronic acid together with cellular material and possibly also trophic factors (US 2002/0197242);
  devices constituted by three-dimensional macrostructures of D,D,L,L-polylactic acid with microstructures of hyaluronic acid as a carrier for BMP (J. Biomed. Matter. Res. 1999, Spring 48(1):95);
  bone grafts formed by porous, three-dimensional matrices similar in structure to sponges, constituted by particles of demineralised bone (WO 02/05750).

SUMMARY OF THE PRESENT INVENTION

The Applicant has found a composite material comprising:
(i) hyaluronic acid and/or hyaluronic acid derivatives,
(ii) a matrix of demineralised bone and/or biocompatible and biodegradable ceramics and/or bone of autologous or allogenic or animal origin.

This material may be used in the preparation of a multilayer composite material containing as the inner matrix the aforementioned composite material which is associated with at least one layer comprising a hyaluronic acid derivative.

In particular the aforementioned composite material and the derived multilayer composite may be used in the preparation of bone substitutes or grafts for the regeneration or formation of bone tissue in surgery.

The present invention therefore relates to bone grafts or bone substitutes consisting of the aforesaid composite material or the derived multilayer composite material.

The present invention further relates to a process for preparing the aforementioned multilayer composite material which comprises the following steps:
  a) forming the inner matrix by associating hyaluronic acid (HA) or a hyaluronic acid (HA) derivative with a matrix of demineralised bone and/or biocompatible and biodegradable ceramics and/or bone of autologous or allogenic or animal origin.
b) coupling said inner matrix with at least one layer comprising a hyaluronic acid (HA) derivative,
c) Fixing the innner matrix to the layer(s) in toto or by means of the outer edge thereof.

DETAILED DESCRIPTION OF THE INVENTION

The substitutes/grafts of bone tissue according to the present invention are absolutely innovative because they are both osteoconductive and osteoinductive, able therefore to induce the process of cellular osteogenesis.

The new bone substitutes/grafts have in fact the following properties:
they are biodegradable and do not produce any substances that are potentially toxic or that may elicit an inflammatory response by the host organism;
they are osteoconductive because they constitute two- and/or three-dimensional structures able to favour cell migration within themselves with a consequent rapid fibrovascularisation by the surrounding tissue;
they can be loaded with cell components of bone marrow, or purified mesenchymal cells (possibly expanded in vitro), undifferentiated, or partially or completely differentiated, in vitro, into osteoblasts and/or osteocytes;
they can contain pharmacologically and/or biologically active ingredients such as antibiotics, steroid and non-steroid anti-inflammatory drugs, antineoplastic agents, cytotoxic and/or cytostatic agents, antiviral agents, cytokines and vitamins;
they prove to be osteoinductive thanks both to their intrinsic characteristics and because they can be loaded with hormones and growth factors that stimulate cell proliferation and/or with factors that favour cell differentiation, or both;
they can be made into any shape or size, so that they can be applied surgically wherever a graft is required;
they can be fixed with surgical thread and/or glued with fibrin or other natural or synthetic glues, or using polymers such as hyaluronic acid and the derivatives thereof.

These bone substitutes/grafts can also be applied surgically in fields other than orthopaedics, such as those listed hereafter:
in spinal surgery;
in maxillofacial surgery;
in surgery to the shoulder, hand and foot;
in dental surgery;
in oncological surgery (in the case of resection and/or emptying of bone tissue);
in all types of orthopaedic surgery requiring the formation of new bone tissue to regenerate damaged or surgically removed bone tissue;
in all types of orthopaedic surgery requiring the fusion of adjacent bones and then the formation of new bone tissue.

Orthopaedic surgery to the spine that may require the application of the bone graft that is the subject of the present invention includes:
fusion of two adjacent vertebral bodies following the fracture/breakage of one of them;
fusion of two adjacent vertebral bodies to correct spinal deformities;
fusion of two vertebral bodies following diskectomy;
fusion of two adjacent vertebral bodies as a surgical solution to the process of one vertebra slipping on the next, with consequent compression of the nerve roots;
filling of one or more vertebral bodies previously hollowed out following infection and/or cancer (that may cause the vertebral bone to degenerate), and subsequent fusion of the two adjacent vertebral bodies.

All the above-listed types of bone graft/fusion can be performed by introducing the graft between the two adjacent vertebrae or in front of and/or behind them, according to the pathology to be surgically treated, as described earlier.

The main components present in the composite material or in the inner matrix of the derived multilayer composite materials which form the new bone substitutes/grafts according to the present invention, are hyaluronic acid (HA) and/or the derivatives thereof, in association with DM or hydroxyapatite and/or tribasic calcium phosphate salts, or, possibly, with granules and/or powders of autologous and/or allogenic bone and/or bone of animal origin.

HA is a hetero-polysaccharide composed of alternate residues of D-glucuronic acid and N-acetyl-D-glucosamine. It is a linear chain polymer with a molecular weight that may vary between 50,000 and $13 \times 10^6$ Da, according to the source from which it is obtained and the methods used to prepare it. It is present in nature in the pericellular gels, in the fundamental substance of the connective tissue of vertebrate organisms (of which it is one of the main components), in the synovial fluid of joints, in the vitreous humor and in the umbilical cord.

HA plays an important role in the biological organism, as a mechanical support for cells in many tissues such as the skin, the tendons, the muscles and the cartilage. The HA used in the present invention may derive from any source, for example it can be extracted from rooster combs (European patent No. 0138572 B1), or it can be obtained by fermentation (European patent application No. 0716688), or by technological means (Italian patent application No. PD94A000042) and its molecular weight can range between 400 and $3 \times 10^6$ Da, in particular between $1 \times 10^5$ Da and $1 \times 10^6$ Da, and more particularly between 200,000 and 750,000 Da.

The HA derivatives that can be used in the formation of the bone substitutes/grafts that are the subject of the present invention are listed hereafter:
1) HA salified with organic and/or inorganic bases;
2) HYAFF®: esters of HA with alcohols of the aliphatic, araliphatic, cycloaliphatic, aromatic, cyclic and heterocyclic series, with a percentage of esterification that may vary according to the type and length of the alcohol used, preferably between 50 and 100%, while the remaining percentage of non-esterified HA may be salified with organic and/or inorganic bases (European patent No. 0216453 B1);
3) HYADD™: amides of HA with amines of the aliphatic, araliphatic, cycloaliphatic, aromatic, cyclic and heterocyclic series, with a percentage of amidation of between 0.1 and 15%, while the remaining percentage of HA which has not undergone amidation may be salified with organic and/or inorganic bases (European patent application publication No. 1095064);
4) O-sulphated HA derivatives to the $4^{th}$ degree of sulphation (European patent No. 0702699 B1);
5) ACP®: inner esters of HA with a percentage of esterification lower than or equal to 20%, preferably between 0.05 and 5%, while the remaining percentage of non-esterified HA can be salified with organic and/or inorganic bases (European patent No. 0341745 B1);
6) Deacetylation products of HA: these derive from the deacetylation of the N-acetyl-glucosamine fraction with a percentage of deacetylation ranging preferably between 0.1 and 30%, while the carboxy groups of HA may be salified with organic and/or inorganic bases (international patent application PCT No. WO 02/18450);

7) HYOXX®: percarboxylated derivatives of HA obtained by the oxidation of the primary hydroxyl of the N-acetyl-glucosamine fraction with a degree of percarboxylation of between 0.1 and 100% and, preferably between 25 and 75%. All the carboxy groups of HA can be salified with organic and/or inorganic bases (international patent application PCT No. WO 02/18448).

The HA derivatives listed above that have proved to be particularly important in forming the new bone grafts are the esters of hyaluronic acid, preferably the benzyl ester (HYAFF™11), esterified to a percentage of between 50 and 100%, and preferably between 75 and 100%.

It is known that HA, main ingredient of the extracellular matrix, modulates many different processes such as proliferation, migration, cell differentiation and angiogenesis through the membrane receptor CD44, and that it also has other functions, such as tissue hydration and joint lubrication.

Moreover, it is known that low-molecular-weight HA fractions have a strong osteoinductive potential with regard to mesenchymal cells (European patent No. 0637245 B1) and that HA is therefore often used to make pharmaceutical formulations (such as filler pastes) possibly also in association with pharmaceutically active ingredients and natural and artificial bone granules to promote the growth and regeneration of damaged bone tissue (European patent No. 637254).

Also known is the use of HA derivatives in the formation of fibres (European patent No. 0618817 B1) which, when made into a non-woven fabric, constitute a three-dimensional matrix that can be used above all in the field of dermatology (in the wound-healing process), thanks to HA's strong capacity for chemotaxis, favouring cell recruitment at the application site.

These non-woven fabrics based on hyaluronic acid derivatives can therefore be defined as osteoinductive in cases where the recruited cells are subsequently destined to differentiate into osteoblasts.

The aforesaid three-dimensional structures can be loaded with mesenchymal cells and maintained in vitro for as long as is necessary to favour cell proliferation and/or differentiation (European patent No. 0863776 B1).

The new bone substitutes/grafts further subject of the present invention are multilayer, composite structures, mainly constituted by hyaluronic acid and the derivatives thereof in association with hydroxyapatite and/or tribasic calcium phosphate, and/or with DM, and/or with bone granules of autologous, allogenic or animal origin.

They are called multilayer because they are composed of at least 2 and preferably 3 layers with the inner matrix consisting of the composite material according to the present invention containing the aforementioned components (i) and (ii), variously assembled and processed, sandwiched between them.

The main component of the above-described layers is a hyaluronic acid derivative (as previously listed), preferably an ester derivative, and more specifically the benzyl ester with a percentage of esterification ranging between 50 and 100%, preferably between 75 and 100%, more preferably in the form as listed below:

a non-woven material, as described in European patent No. 0618817 B1, containing fibres of the hyaluronic acid ester, possibly associated with other natural polymers such as collagene and cellulose or derivatives thereof, or synthetic polymers such as poly-lactic acid, poly-glycolic acid and poly-caprolactone acid;

a woven material containing fibres constituted by the hyaluronic acid ester, possibly subsequently immersed in a solution of HA according to European patent No. 0625056 B1;

esters made into the form of compact, porous microporous or perforated membranes and films (European patent No.0462426 B1).

The aforementioned films may also be of another HA derivative, such as those listed above.

The matrix inside the structure claimed by the present Applicant, may be constituted by 2 or more components and may therefore be in the form of a composite association of materials that are listed and described below:

HA sodium salt, with a molecular weight of between 30 KD and $1.5 \times 10^3$ KD, preferably from 200 KD to 750 KD;

HA derivatives such as esters (HYAFF®), inner esters (ACP®), percarboxylated derivatives (HYOXX®), amides (HYADD™), sulphated and deacetylated HA derivatives. Said derivatives may be made into the form of fibres, powders, microspheres, sponges, pastes, gels and granules;

bone matrix, totally or partially demineralised (DM);

biodegradable, biocompatible and bioabsorbable materials such as hydroxyapatite, tribasic calcium phosphate and calcium sulphate;

bone granules and/or powders of autologous, allogenic or animal origin, of various shapes and sizes.

The abovesaid materials can be associated with one another in many different ways:

1) sponges preferably constituted by the benzyl ester of hyaluronic acid (European patent No. 0216453 B1) with a percentage of esterification ranging between 70 and 100%, containing within them bone granules or powders that are autologous and/or allogenic and/or of animal origin, or granules or other two- or three-dimensional structures constituted by biodegradable ceramics or, lastly, sponges containing DM.

2) sponges according to point 1, subsequently coated throughout with HA and/or the derivatives thereof in the form of a thin film and/or sponge, to favour the entry, distribution and adhesion of the cells that will migrate once they have been loaded therein.

3) sponges formed by the inner esters of HA (ACP®) containing between them bone granules and/or powders autologous and/or allogenic and/or of animal origin, or constituted by biodegradable ceramics or, lastly, sponges of ACP® containing DM.

4) granules, spheres, powders and/or two- and three-dimensional structures of various shapes and sizes constituted by biodegradable ceramics that are coated/incorporated in a layer of HA subsequently cross-linked to form its inner ester (ACP®) which thus covers all the ceramic structures described above.

5) pastes and/or gels constituted by HA derivatives enclosing bone powders and/or granules that are autologous and/or allogenic and/or of animal origin, or granules or other two- or three-dimensional structures constituted by biodegradable ceramics or, lastly, pastes and/or gels containing DM;

6) fibres constituted by the benzyl ester of HA (HYAFF® 11) (possibly also associated with other natural polymers and with the derivatives thereof such as collagen and cellulose, or synthetic polymers such as poly-lactic, polyglycolic and poly-caprolactone acid) with a percentage of esterficiation ranging between 50 and 100%, preferably 75% (HYAFF®11p75), in association with DM and hyaluronic acid, preferably sodium salt, for the formation of a compact paste as a matrix to insert between two layers as described earlier. The matrix can be wetted with a solution of HYAFF®, to render it more compact with the layers between which it is sandwiched. The percentage of said matric composed of fibres of HYAFF® 11p75 may vary between 10 and 50%, but is preferably between 14 and 24%. The percentage of DM in the composition of the matrix may vary between 50 and 90%, preferably between 60 and 80%. The hyaluronic acid present in the final composition may have a molecular weight ranging from 200 to 750 KD, preferably from 500 to 700 KD, and may be present at a percentage varying between 0.1 and 40%, preferably between 5 and 10%.

All the above matrices can then be immersed in polymers of various kinds to make the final matrix more compact and to fix them to the layer/s.

The polymers chosen for their soaking and fixing qualities are the following:

HYAFF® 11 with a percentage of esterification of between 55 and 100%;

fibrin glue, photocross-linkable polymers (international patent application No. WO 03/076475), collagen and derivatives.

When thermoplastic polymers such as poly-lactic and poly-glycolic acid or poly-caprolactone acid are used, all the above matrices can be fixed to the previously described layer/s by a process of heat treatment of the outer edges to prevent the "sandwich" from coming apart.

Conversely, when materials other than thermoplastic polymers are used, the matrices may undergo a needle-punching process, together with the layers they are to be sandwiched between (European patent No. 0618817 B1). Said process can be performed only on the outer edges of the "sandwich" or on the whole, multilayer structure. The needle-punching process is possible when thermoplastic polymers are used too, in which case it can be performed at a high temperature to create fusion points between the different fibres.

Lastly, the structures can also be sewn with suture thread based on HYAFF® or another biocompatible and bioabsorbable polymer.

The multilayer, composite structures that are the subject of the present invention can also take the form of three-dimensional, bag-shaped structures intended as fillers for vertebral bodies that have been surgically emptied following infections or cancer, or for use in all types of orthopaedic surgery requiring the formation of new bone tissue for the regeneration of tissue that has been damaged or surgically removed.

All the composite materials according to the present invention can be loaded with bone marrow cells taken from the patient directly in the operating theatre while undergoing the type of orthopaedic surgery that requires their application, or a few days before the graft is due to be performed, to allow the purification and expansion in vitro of the mesenchymal cells in the marrow, so that these can then be loaded into the structure that is the subject of the present invention, either undifferentiated and/or partially or completely differentiated into osteoblasts/osteocytes.

Alternatively, said new composite structures can also be loaded with allogenic bone marrow cells, possibly purified, expanded and differentiated in vitro.

For purely descriptive purposes, we report hereafter some examples of the preparation of the multilayer, composite structures that are the subject of the present invention:

EXAMPLE 1

Preparation of the Compact Films Constituted by HYAFF® 11 as the Outer Layer/s of the New Multilayer, Composite Structures One liter of a solution of HYAFF® 11 in DMSO (European patent No. 0216453 B1) is prepared at a concentration of 150 mg/ml.

Using a geared metering pump, the solution is passed through an extruder with a slit 20 cm long and 200 µm wide; the extruder is immersed in a coagulating bath constituted by 10 liters of ethanol-water at a ratio of 90:10.

The solid film that is formed is then passed into two subsequent baths filled with, respectively, ethanol-water at a ratio of 80:20 and ethanol alone.

Lastly, the film is dried and cut to size.

EXAMPLE 2

Preparation of Sponges of Hyaff® 11 Containing Granules of Hydroxyapatite and/or DM and/or Other Different Biocompatible and Biodegradabile Ceramics 230 g. of sodium chloride crystals with a granule size of between 200 and 350 µm is mixed with 6.6 g. of citric acid with a granule size of less than 200 µm and with 8.5 g. of bicarbonate of soda with a granule size of between 140 and 400 µm.

The mixture is then supplemented with 20 g. of resorbable hydroxyapatite in granules sized 200-250 µm (or more), and/or DM and/or tribasic calcium phosphate and/or calcium sulphate.

Said mixture of salts is then further supplemented with 60 ml of a solution of HYAFF® 11 in DMSO at a concentration of 180 mg/ml, and the components are mixed for at least 1 hour.

The paste thus obtained is spread into flat shapes measuring, for example 5×15 cm, with a thickness, for example, of between 2 and 5 mm, preferably 3 mm. Said shapes are then sprinkled with a mixture of salts constituted by:

100 g. of particulate NaCl with a granule size of less than 200 µm, 38-40 g. of particulate citric acid with a granule size of less than 200 µm, 50-55 g. of particulate bicarbonate of soda with a granule size of less than 200 µm.

The product thus obtained is subsequently immersed for at least 1 hour in a solution constituted by water-ethanol at a ratio of 70:30.

The product is then washed repeatedly in water to eliminate the sodium chloride (NaCl) completely. The sponges thus obtained are subsequently freeze-dried.

EXAMPLE 3

Preparation of Sponges of Hyaff® 11 Containing Granules of Hydroxyapatite Subsequently Coated/Incorporated by HYAFF® 11

Once the sponges have been prepared as described Example 2, and before they are freeze-dried, the product is immersed in 1 liter of solution constituted by HYAFF® 11 esterified to a degree of 50% (HYAFF® 11p50) in water at a concentration of 9 g./l. Subsequently, said solution is depressurised with a vacuum pump set at a pressure of less than 800 mbar for at least 0.5 minutes then returned to ambient pressure.

This cycle is repeated at least 5 times.

The material thus obtained is freeze-dried.

EXAMPLE 4

Preparation of Composite Matrices of Hydroxyapatite and/or of Bone Structures, Containing/Incorporating Cross-Linked Hyaluronic Acid (Acp®)

1.9-2 g. of hyaluronic acid salified with phenyl trimethylammonium is solubilised in 27-30 ml of water.

A varying number (between 12 and 18) of resorbable and porous hydroxyapatite and/or bone structures (measuring, for example, 10×10×10 mm), are placed together in a tray with sides sufficiently high to contain a solution of hyaluronic acid, prepared as described above, which is poured over the hydroxyapatite until it is completely submerged.

Said solution containing hydroxyapatite and/or bone tissue derivatives is de-pressurised with a vacuum pump set at less than 600 mbar for at least 0.5 minutes.

The above-described cycle is repeated at least 5 times.

Subsequently, freeze-drying is performed as follows:

the product obtained is brought to a temperature of −4° C.

the temperature is further lowered to at least −25° C.

the freeze-drying chamber is depressurised to a pressure of less than 10 mbar, then the product obtained is heated to a temperature of 30° C. to eliminate its initial water content completely.

The freeze-dried product is placed in a glass reactor with a cooling system, to which 150 ml of acetone and 1 g. of CMPI (chloro-methyl-pyridinium iodide) has been added.

It is heated to 62° C. for 12 hours, to obtain a product constituted by pieces of hydroxyapatite incorporated into/ or coated by a sponge of cross-linked hyaluronic acid (ACP®) which must immediately be washed in 3% ammonium acetate, ethanol, in 3% sodium chloride, and lastly in ethanol/water again to eliminate all traces of the sodium chloride.

The product is then dried in a flow of nitrogen for at least 8 hours, and subsequently placed in a vacuum for at least 8 hours.

EXAMPLE 5

Preparation of Composite Matrices Containing Hyaluronic Acid Associated with DM and/or Hydroxyapatite and/or a Biocompatible and Biodegradable Ceramic A solution is prepared that is constituted by 375 mg of hyaluronic acid in 25 ml of phosphate buffer at pH 7.2.

The solution is mixed with 8 grams of DM and/or hydroxyapatite and/or other biocompatible and biodegradable ceramics in the form of granules with a granule size of 2 mm.

The matrix thus formed is poured into a container measuring 10×10 cm and is ready to be freeze-dried.

The spongy structure thus obtained is placed between two layers of non-woven fabric constituted by HYAFF®11p80.

The multilayer structure then undergoes a needle-punching process (as described in European patent No. 0618817 B1), to enable and favour the joining of the two layers of non-woven fabric and the matrix between them.

EXAMPLE 6

Preparation of Multilayer, Composite Structures in the Final Stage of Assembly and Fixing of the Inner Matrix With the External Layer.

Having prepared the matrix as described in examples 2, 3 and 4, it is wetted with ethanol and a thin layer of HYAFF® 11 in DMSO at a concentration of 50 mg/ml is spread over the surfaces.

The surfaces thus prepared are then coated with the material of choice (non-woven fabric, or tissue or film, preferably of HYAFF® 11), exerting slight pressure on it.

The product is then immersed in a bath of ethanol-water 80:20 for 1 hour and then washed repeatedly with pure ethanol.

The final composite product is washed in water and freeze-dried.

EXAMPLE 7

Preparation of Multilayer, Composite "Sandwich" Structures, Whose Inner Matrix Contains HYAFF®, Hyaluronic Acid and DM 3.6 g. of HYAFF® 11p75 fibre is mixed for at least 10 minutes with 84 cc of a solution constituted by hyaluronic acid in an aqueous solution with a concentration of 18-19 mg/ml. Said mixture is supplemented with 20 g. of granules of DM and kneaded for at least 15 minutes. The paste thus obtained is subsequently spread into squares measuring, for example, 10×10 cm with a thickness of 2-3 mm.

The inner matrix thus formed is placed between 2 layers of HYAFF® 11, made into a non-woven or woven fabric, having equal dimensions and the composite multi-layer product obtained is calendered and finally freeze-dried.

The freeze-dried pieces can be cut to size.

At this point, the pieces can be treated by one or other of the following procedures:

1) both of them can be immersed in a solution of HYAFF® 11p75 in DMSO with a concentration of 20-25 mg/ml for several minutes.
2) The edges of each piece can be wetted with a solution of HYAFF® 11 in DMSO (with a concentration of 30-40 mg/ml) and subsequently immersed in an ethanol bath for at least 10 minutes.

The pieces treated as described in point 1 and those treated as described in point 2 are both washed twice for at least 1 hour (under mechanical stirring) with 1 liter of a solution formed by ethanol and water at a ratio of 80:20, then with pure ethanol and finally dried.

EXAMPLE 8

Preparation of Mnultilayer, Composite "Bag-Shaped" Structures 3.6 g. of HYAFF®11p75 fibres are mixed for at least 10 minutes with 84 cc of a solution constituted by hyaluronic acid in an aqueous solution with a concentration of 18-19 mg/ml. Said mixture is supplemented with 20 g. of granules of DM and kneaded for at least 15 minutes. The paste thus obtained is inserted in a woven, tubular structure, preferably made of HYAFF®11, and freeze-dried.

The edges are then wetted with a solution of HYAFF®11 in DMSO with a concentration equal to 35 mg/ml, and then immersed in an ethanol bath for at least 10 minutes.

The product thus obtained is washed in ethanol-water at a ratio of 80:20 for at least 1 hour, then again in pure ethanol and, lastly, dried.

The invention being thus described, it is clear that these methods can be modified in various ways. Such modifications are not to be considered as divergences from the spirit and purpose of the invention and any modification that would appear evident to an expert in the field comes within the scope of the following claims.

The invention claimed is:

1. An osteoconductive and osteoinductive multilayer composite material comprising:
   (I) an inner matrix composite material comprising:
      (i) hyaluronic acid and a hyaluronic acid derivative, wherein said hyaluronic acid derivative is in a form selected from the group consisting of a non-woven material, a woven material, a compact membrane or film, and a perforated membrane or film; and
      (ii) demineralised bone and/or biocompatible and biodegradable ceramic and/or bone of autologous or allogenic or animal origin, and
   (II) at least two layers, each layer comprising a hyaluronic acid derivative, wherein the hyaluronic acid derivatives in (I)(i) and (II) are each selected from the group consisting of:
      (a) an ester of hyaluronic acid,
      (b) an inner ester of hyaluronic acid,
      (c) an amide of hyaluronic acid,
      (d) an O-sulphated derivative of hyaluronic acid,
      (e) a deacetylated derivative of hyaluronic acid, and
      (f) a percarboxylated derivative of hyaluronic acid, and
   wherein said at least two layers (II) are superimposed on said inner matrix (I) thereby sandwiching said inner matrix (I) between said layers (II).

2. The multilayer composite material of claim 1, wherein the hyaluronic acid in (i) is a hyaluronic acid salified with an organic or inorganic base.

3. The multilayer composite material of claim 1, wherein said hyaluronic acid derivative is a benzyl ester of hyaluronic acid.

4. The multilayer composite material of claim 3, wherein the benzyl ester has a degree of esterification of from 50% to 100%.

5. The multilayer composite material of claim 4, wherein the benzyl ester has a degree of esterification of from 75% to 100%.

6. The multilayer composite material of claim 1, wherein said hyaluronic acid derivative is the hyaluronic acid inner ester having an esterification degree lower than 20%.

7. The multilayer composite material of claim 6, wherein the hyaluronic acid inner ester has an esterification degree between 0.05% and 5%.

8. The multilayer composite material of claim 1, wherein said hyaluronic acid derivative is the amide of hyaluronic acid having an amidation degree of lower than or equal to 15%.

9. The multilayer composite material of claim 8, wherein the amidation degree is between 0.1% and 15%.

10. The multilayer composite material of claim 1, wherein said hyaluronic acid derivative is the deacetylated hyaluronic acid having a percentage of deacetylation lower than or equal to 30%.

11. The multilayer composite material of claim 1, wherein said hyaluronic acid derivative is the percarboxylated hyaluronic acid (f) having a percarboxylation degree of between 0.1% and 100%.

12. The multilayer composite material of claim 11, wherein said percarboxylation degree is between 25% and 75%.

13. The multilayer composite material of claim 1, wherein the biocompatible and biodegradable ceramics are selected from the group consisting of hydroxyapatite, anhydrous tribasic calcium phosphate, and calcium sulphate.

14. The multilayer composite material of claim 1, wherein the demineralised bone is a partially or completely demineralised bone matrix.

15. The multilayer composite material of claim 1, wherein the hyaluronic acid derivative has a molecular weight of between 200 and 750 KD.

16. The multilayer composite material of claim 1, wherein the hyaluronic acid derivative in the inner matrix (I) is in a form selected from the group consisting of a sponge, a paste, a gel, a granule, and a powder.

17. The multilayer composite material of claim 1, wherein said at least two layers (II) comprises two layers.

18. The multilayer composite material of claim 1, wherein said at least two layers (II) comprises three layers.

19. The multilayer composite material of claim 1, wherein the inner matrix (I) is in the form of a sponge consisting of the benzyl ester of hyaluronic acid having a percentage of esterification between 70% and 100%, containing inside said sponge: bone granules or powders; or granules or other three-dimensional structures containing said biodegradable ceramics; or said partially or completely demineralised bone matrix.

20. The multilayer composite material of claim 1, further comprising a coating of said hyaluronic acid and/or derivatives thereof said composite material in the form of a thin film and/or sponge, to favour entry, distribution, and adhesion of cells that will migrate when said cells are loaded therein.

21. The multilayer composite material of claim 1, wherein the inner matrix is in the form of a sponge formed by the inner esters of hyaluronic acid, the inner matrix containing partially or completely demineralised bone matrix; biocompatible and biodegradable ceramic; or bone in the form of granules and/or powders and of autologous or allogenic or animal origin.

22. The multilayer composite material of claim 1, wherein the inner matrix is in the form granules, spheres, powders, and/or three-dimensional structures of various shapes and sizes, the matrix consisting of biodegradable ceramics that are coated or incorporated with a layer of hyaluronic acid which is cross-linked into the inner ester of said layer of hyaluronic acid, thereby covering all the biodegradable ceramics.

23. The multilayer composite material of claim 1, wherein the inner matrix is in the form of pastes and/or gels containing demineralised bone matrix; granules or other three-dimensional structures containing biocompatible and biodegradable ceramics; or pastes and/or gels consisting of said hyaluronic acid and hyaluronic acid derivatives enclosing bone powders and/or granules that are autologous or allogenic or of animal origin.

24. The multilayer composite material of claim 1, wherein the inner matrix is in the form of fibres comprising the benzyl ester of hyaluronic acid having a percentage of esterification between 50% and 100%, the inner matrix optionally associated with other natural polymers selected from the group consisting of collagen, and cellulose, or synthetic polymers selected from the group consisting of poly-lactic, polyglycolic, and poly-caprolactone acid, and wherein said natural or synthetic polymers are in association with demineralized bone matrix and hyaluronic acid.

25. The multilayer composite material of claim 1, wherein the matrix is wetted with a solution of the hyaluronic acid ester, to compact the matrix between the layers in which said matrix is sandwiched.

26. The multilayer composite material of claim 1, wherein said matrix consists of fibres of hyaluronic acid benzyl ester having an esterification degree of 75% and in an amount in the composite material from 10% to 50%; demineralised bone matrix in an amount from 50% to 90%; and hyaluronic acid having an average molecular weight ranging from 200 to 750 KD, in an amount from 0.1% to 40%.

27. The multilayer composite material of claim 26, wherein said matrix consists of fibres of hyaluronic acid benzyl ester having an esterification degree of 75% in an amount in the composite material from 14% to 24%; demineralised bone matrix in an amount between 60% and 80%; and hyaluronic acid having an average molecular weight from 500 to 700 KD in an amount between 5% and 10%.

28. The multilayer composite material of claim 1, wherein said inner matrix is immersed in a solution to compact the matrix and to fix the matrix to the layers (II).

29. The multilayer composite of claim 28, wherein said composition further comprises a polymer selected from the group consisting of a hyaluronic acid benzyl ester with a percentage of esterification of between 55% and 100%; a fibrin glue; a photocrosslinikable polymer; and collagen.

30. The multilayer composite material of claim 1, wherein said at least two one or more layers (II) comprises hyaluronic acid ester.

31. The multilayer composite material of claim 30, wherein said hyaluronic acid is the benzyl ester having a percentage of esterification between 50% and 100%.

32. The multilayer composite material of claim 31, wherein said percentage of esterification is between 75% and 100%.

33. The multilayer composite material of claim 30, wherein the layers (II) are in the form of a non-woven material, containing fibres of the hyaluronic acid ester and optionally associated with a natural polymer selected from the group consisting of collagen and cellulose, or a synthetic polymer selected from the group consisting of poly-lactic acid, poly-glycolic acid, and poly-caprolactone acid.

34. The multilayer composite material of claim 30, wherein the layers (II) are in the form of a woven material containing fibres of the hyaluronic acid ester, optionally immersed in a solution of hyaluronic acid.

35. The multilayer composite material of claim 1, wherein the layers are in the form of a compact, perforated porous or microporous membrane or film.

36. The multilayer composite material of claim 1, further containing a pharmacologically and/or biologically active ingredient.

37. The multilayer composite material of claim 36, wherein the pharmacologically active ingredient is selected from the group consisting of antibiotics, antineoplastics, anti-inflammatories, cytokines, vitamins, and cytotoxic, cytostatic and antiviral agents.

38. The multilayer composite material of claim 36, wherein biologically active ingredients contain trophic, osteoinductive, and/or angiogenetic factors.

39. The multilayer composite material of claim 38, wherein the trophic, osteoinductive, and/or angiogenetic factors are selected from the group consisting of bone morphogenetic protein, transforming growth factor, platelet derived growth factor, fibroblast growth factor, epidermal growth factor, insulin-like growth factor, and vascular endothelial growth factor.

40. A bone substitute or graft consisting of the multilayer composite material of claim 1.

41. The bone substitute or graft of claim 40, wherein the graft is in the form of a sandwich or bag.

42. The multilayer composite material of claim 1, wherein the hyaluronic acid derivative is in the form of fibres.

43. The multilayer composite material of claim 1, wherein the inner matrix (I) is in the form of a paste.

44. The multilayer composite material of claim 1, wherein the at least two layers (II) comprise the hyaluronic acid derivative in the form of a woven material.

45. The multilayer composite material of claim 1, wherein said inner matrix (I) comprises said hyaluronic acid derivative in an amount between 10% and 50%; said demineralised bone and/or biocompatible and biodegradable ceramic and/or bone of autologous or allogenic or animal origin in an amount between 50% and 90%; and said hyaluronic acid in an amount between 0.1% and 40%.

46. The multilayer composite material of claim 45, wherein the inner matrix (I) comprises said hyaluronic acid derivative in an amount between 14% and 24%; said demineralized bone and/or biocompatible and biodegradable ceramics and/or bone of autologous or allogenic or animal origin in an amount between 60% and 80%; and said hyaluronic acid in an amount between 5% and 10%.

47. The multilayer composite material of claim 1, wherein the inner matrix (I) is in the form of a paste comprising a benzyl ester of hyaluronic acid in the form of fibres, hyaluronic acid, and demineralised bone, and wherein the at least two layers (II) comprise the hyaluronic acid derivative in the form of a woven material.

* * * * *